United States Patent [19]

Gnabre

[11] Patent Number: 5,989,555
[45] Date of Patent: Nov. 23, 1999

[54] EXTRACTS OF *LARREA TRIDENTATA* HAVING ANTIVIRAL ACTIVITY AND THEIR USE FOR TREATING VIRAL INFECTIONS

[76] Inventor: John N. Gnabre, 6 Dalmeny Ct., #201, Baltimore, Md. 21234

[21] Appl. No.: 08/641,850

[22] Filed: May 2, 1996

Related U.S. Application Data

[60] Provisional application No. 60/009,673, Jan. 5, 1996.

[51] Int. Cl.$^6$ .......................... A01N 65/00; A01N 27/00; C07C 209/00
[52] U.S. Cl. ...................... 424/195.1; 514/766; 514/934; 564/280
[58] Field of Search .................. 424/195.1; 514/766, 514/934; 564/280

[56] References Cited

U.S. PATENT DOCUMENTS 4,774,229  9/1988  Jordan ........................................ 514/25

OTHER PUBLICATIONS

Gnabre et al., Tetrahedron, 51, No. 45, pp. 12203–12210 (1995).
Gisvold et al., J. of Pharm. Sciences, 63, No. 12, pp. 1905–1907 (1974).
Perry et al., J. Org. Chem., 37, No. 26, pp. 4371–4376 (1972).
MacRae et al., Phytochemistry, 23, No. 6, pp. 1207–1220 (1984).
*Lignans: Chemical, Biological & Clinical Properties*, Ayres and Loike, Eds. pp. 85–112 (Copyright 1990 by Cambridge Univ. Press, NY).
US/IBP Synthesis Series, *Creosote Bush—Biology and Chemistry of Larrea in New World Deserts*, Mabry, Hunziker & DiFeo, Eds., (Copyright 1977 by The Institute of Ecology) Chapter 5, pp. 115–134.
ACS HCAPLUS 1995:789132 Fujihashi et al WO 9501950, Jan. 1995.
Derwent Abs 95–074909—Tanaka et al—WOO9501950 Jan. 19, 1995.

*Primary Examiner*—Herbert J. Lilling
*Attorney, Agent, or Firm*—Birch, Stewart, Kolasch & Birch, LLP

[57] ABSTRACT

*Larrea tridentata* and *Ambrosia deltoidea* are shown to produce compounds that inhibit replication of HIV. The compounds can be extracted by differential fractionation and by counter-current chromatographic methods described herein. Extracts prepared from *L. tridentata* and *A. deltoidea* are found to be effective in inhibiting viral replication. The extracts from *L. tridentata* have been characterized and found to contain tricyclic lignans. The extracts can be administered to subjects for treatment of viral infection.

9 Claims, 15 Drawing Sheets

60%

20%

10% (ayanin)

80%

80% (Mal.4)

20%

60%

R = H, Me, or acetate

R = H, OH, or OMe

R = H, OH, or OMe

HIV-1 TRANSCRIPTION *IN VITRO*
(Gene Expression, 2 (4): 391-407, 1992)

EXTRACTS OF *LARREA TRIDENTATA* HAVING ANTIVIRAL ACTIVITY AND THEIR USE FOR TREATING VIRAL INFECTIONS

RELATED APPLICATIONS

The present application is related to a copending application by Ru Chih C. Huang and John N. Gnabre, entitled "Compounds for the Suppression of HIV Tat Transactivation", U.S. Ser. No. 08/316,341, filed Sep. 30, 1994, the entire contents of which are hereby incorporated by reference. This application claims priority of the U.S. provisional application Ser. No. 60/009,673, filed Jan. 5, 1996.

BACKGROUND OF THE INVENTION

1. Field of the Invention

The present invention is directed to extracts from the leaves and flowers of the creosote bush (*Larrea tridentata*, Zygophyllaceae) having anti-HIV activity. The extracts of at least *L. tridentata* contain a variety of tricyclic compounds, including cyclolignan compounds, which are also the subject matter of the present invention. The invention also embraces derivatives and isomers of the tricyclic compounds found in the extracts. Finally, the present invention also encompasses methods for treating retroviral infections, especially HIV infection, by administering the extract and/or purified tricyclics or cyclolignans to an HIV-infected subject.

2. Description of the Related Art

Articles of the scientific literature cited throughout this application are hereby incorporated by reference in their entirety by such citation.

It is becoming clear that control or cure of HIV infection in a subject will require a multifacetted approach, which partly relies upon inhibition of the HIV replication cycle. Furthermore, it is clear that a several aspects of viral replication will have to be attacked. For instance, it has recently been shown that a regimen of multiple drugs, such as inhibitors of reverse transcriptase (RT), AZT, ddI, and the protease inhibitor, 3TC, has proved more effective in controlling the virus than administration of any one of these drugs alone.

It has been shown that the creosote bush and related species contain active principles with antimicrobial and antiviral activity (Ayres et al., Ch. 3, p. 85 in *Lignans: Chemical, Biological and Clinical Properties—(Chemistry and Pharmacology of Natural Products)*, Ayres and Loike, Eds., c. 1990 by Cambridge University Press, New York,).

Tat is a transactivator of human immunodeficiency virus (HIV) gene expression. Tat and Rev are indispensable viral regulatory factors for HIV gene expression. Tat acts by binding to the TAR RNA element and activating transcription from the long terminal repeat (LTR) promoter of the HIV-1 proviral DNA.

It has been shown that upon infection with AIDS virus, basal viral gene transcription is initiated. Activation of viral genes occurs upon antigenic stimulation and results in a burst of viral replication. Expression of the tat gene has been shown to result in several thousand-fold increased levels of HIV LTR-driven gene expression at both the transcriptional and postranscriptional levels.

The Tat protein stabilizes elongation of transcription complexes and has also been shown to be involved in transcription initiation. Previous studies have shown that Tat mediates reduction of antibody-dependent T cell proliferation, contributing substantially to the failure of the immune response. Tat also directly stimulates the growth of Kaposi's sarcoma cells. Tat is indirectly involved in HIV-related dementia in patients with advanced AIDS.

Since Tat has no apparent cellular homologs, this strong positive regulator has become an attractive target for the development of anti-AIDS drugs (see FIG. 1). Currently available AIDS drug such as HIV reverse transcriptase inhibitors (AZT, DDI) or the protease inhibitor (3TC) target viral gene products (enzymes and specific viral proteins). These drugs are capable of suppressing the replication of a wild-type AIDS virus. However, they are ineffective in destroying a small pool of coexisting mutant viruses which continue to replicate at a high rate in the presence of these drugs. An inhibitor which targets Tat transactivation and viral gene transcription at the level of integrated proviral DNA will arrest the virus at an early stage (Hsu et al., *Science*, 254:1799–1802, 1991). Because replication of the viral genome is suppressed, virtually no viral resistance to the drug should develop.

Efforts aimed at the elucidation of factors which control gene expression at the transcriptional and post-transcriptional levels in host eukaryotes have recently made possible quantitative assessment of Tat function (Sim, *Ann. N.Y. Acad. Sci.,* 616:64–70, 1990).

The HIV-1 integrase (HIV-1 IN) mediates the integration of the transcribed viral DNA into the host chromosome, a crucial step in the HIV replication cycle. This enzyme has no known cellular homolog, and relatively simple in vitro assay systems have enabled functional characterization and the screening of specific inhibitors of the HIV-1 IN. Therefore HIV-1 IN has also become a major target for the development of specific anti-AIDS drugs.

SUMMARY OF THE INVENTION

The extracts and compounds of the present invention exhibit activity as inhibitors of Tat-dependent transcription of HIV-1 from the LTR (Tat-TRS inhibitory activity). Among several plant extracts prepared from rain forest and desert medicinal plants used in traditional medicinal against viral affections, only 3-Mag extract obtained from the total extract of the leaves and flowers of the creosote bush *L. tridentata* showed Tat-TRS inhibitory activity (FIG. 2). This extract also inhibits HIV cytopathic effects on human lymphoblastoid cells chronically infected with the virus as assessed by the newly developed soluble-formazan assay (Weislow et al., *J. Natl. Cancer Inst.,* 81: 577–586, 1989).

Furthermore, the present invention encompasses the cyclolignans of the general formula (I). These compounds are called collectively "Rev. 10:7" compounds:

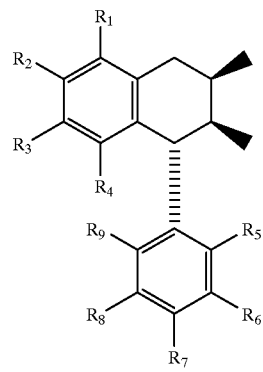

where $R_1$ to $R_9$ are each selected from the group consisting of hydrogen, —OH, —OCH$_3$ (—OMe), other O-lower alkyl, —O(C=O)CH$_3$, —O(C=O)CH$_2$—CH$_3$, provided that $R_1$ to $R_9$ are not all —OH simultaneously. The compounds wherein $R_2$ is —OH, $R_3$ is —OMe or —OH, and all other R groups are H, wherein $R_2$ is —OH, $R_3$ is —OH, $R_6$ is —OMe and all other R groups are H, or wherein each of $R_2$, $R_3$ and $R_6$ are —OH and all other R groups are H, being tricyclics in the prior art, are also not considered purified compounds of the present invention. However, a composition containing one or more of those compounds, especially one that comprises additional tricyclics and/or other compounds extracted from L. tridentata and use of the purified compounds or extracts in the treatment of viral infection is considered within the scope of the invention. The cyclolignans of the invention are present in extracts comprising the cyclolignans which extracts also are part of the present invention.

The present invention also encompasses tricyclic flavones having the general formula shown in FIG. 8c.

BRIEF DESCRIPTION OF THE DRAWINGS

FIG. 1 indicates different steps of HIV replication and the sites of action of potential inhibitors. The steps in viral replication are; 1) Attachment, 2) Uncoating, 3) Reverse Transcription, 4) RNaseH Degradation, 5) DNA Synthesis of Second Strand, 6) Migration to Nucleus, 7) Integration, 8) Latency, 9) Viral Transcription, 10) RNA Processing, 11) Protein Synthesis, 12) Protein Glycosylation, 13) Assembly of Virus, 14) Release of Virus, 15) Maturation, and 16) Other. 3-Magi extract presumably acts at viral attachment (step 1), viral DNA integration (step 7) and at viral transcription (step 9). The sites of action of cyclolignans are 1, 7, 9, and 15. The cyclolignans, Rev.10:7, act at viral transcription (step 9). FIG. 1 indicates the basal transcription step and the viral regulatory protein-dependent transactivation step. Both 3-Magi and Rev.10:7 inhibit these two steps.

Figure 4A:
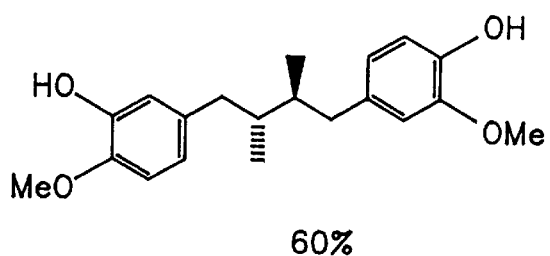
Figure 4B:
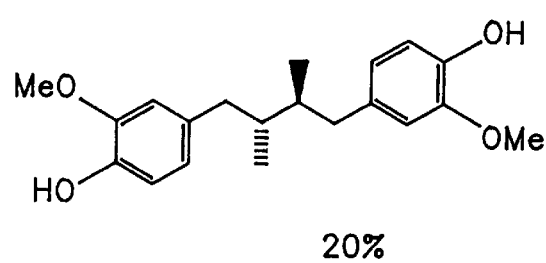
Figure 4C:
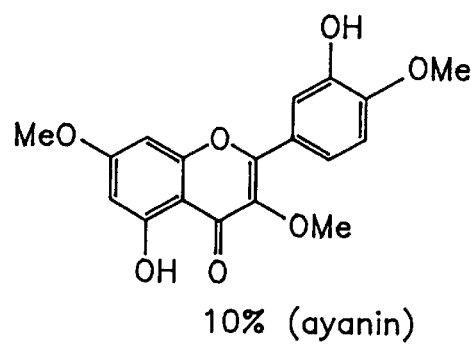
Figure 4D:
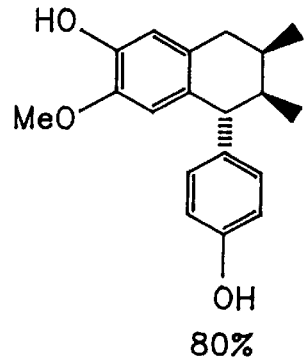

| Component | Fraction No. | Dry weight (mg) | Composition |
|---|---|---|---|
| A | 39–40 | 4.1 | see FIG. 4A |
| B | 46–49 (Rev. 10:7) | 7.6 | see FIG. 4B, remainder is small amounts of type 2 lignans |
| C | 55–58 | 3.6 | 80% flavones, 20%, 4-hydroxybenzene propanoic acid, methyl ester |
| D | 60–66 (Mal.4) | 4.6 | see FIG. 4C |
| E | 70–73 | 5.5 | mixture of type 1 and type 2 lignans |
| F | 76–80 | 0.8 | type 2 lignans |
| G | 85–88 | 1.9 | complex lignan mixture |
| H | 105–120 | 1.5 | see FIG. 4D, also includes aromatics |
| I | 125–140 | 1.8 | aromatics |
| J | 145–160 | 1.3 | not determined |

Figure 4E:
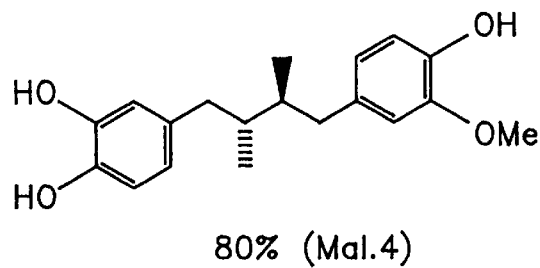
Figure 4F:
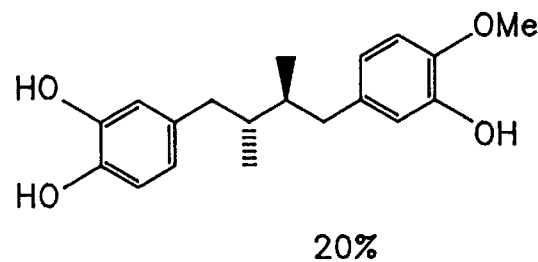
Figure 4G:
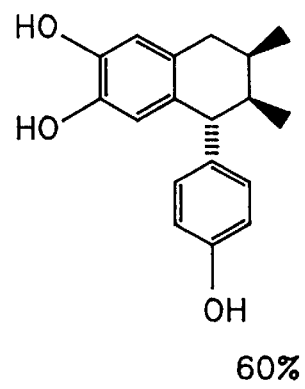

FIGS. 4A–4D show the chemical characterization of the components of select peaks from the CCC chromatogram. Components were analyzed by GC-Mass spectroscopy using an analytical non-destructive capillary column (HP-5, cross-linked 5% phenylmethylsiloxane), and by NMR. FIGS. 4A–4C show the compounds present in fraction A; FIG. 4D shows the compounds present in fraction B; FIGS. 4E–F show the compounds present in fraction D and FIG. 4G shows the compounds present in fraction H.

Figure 5:
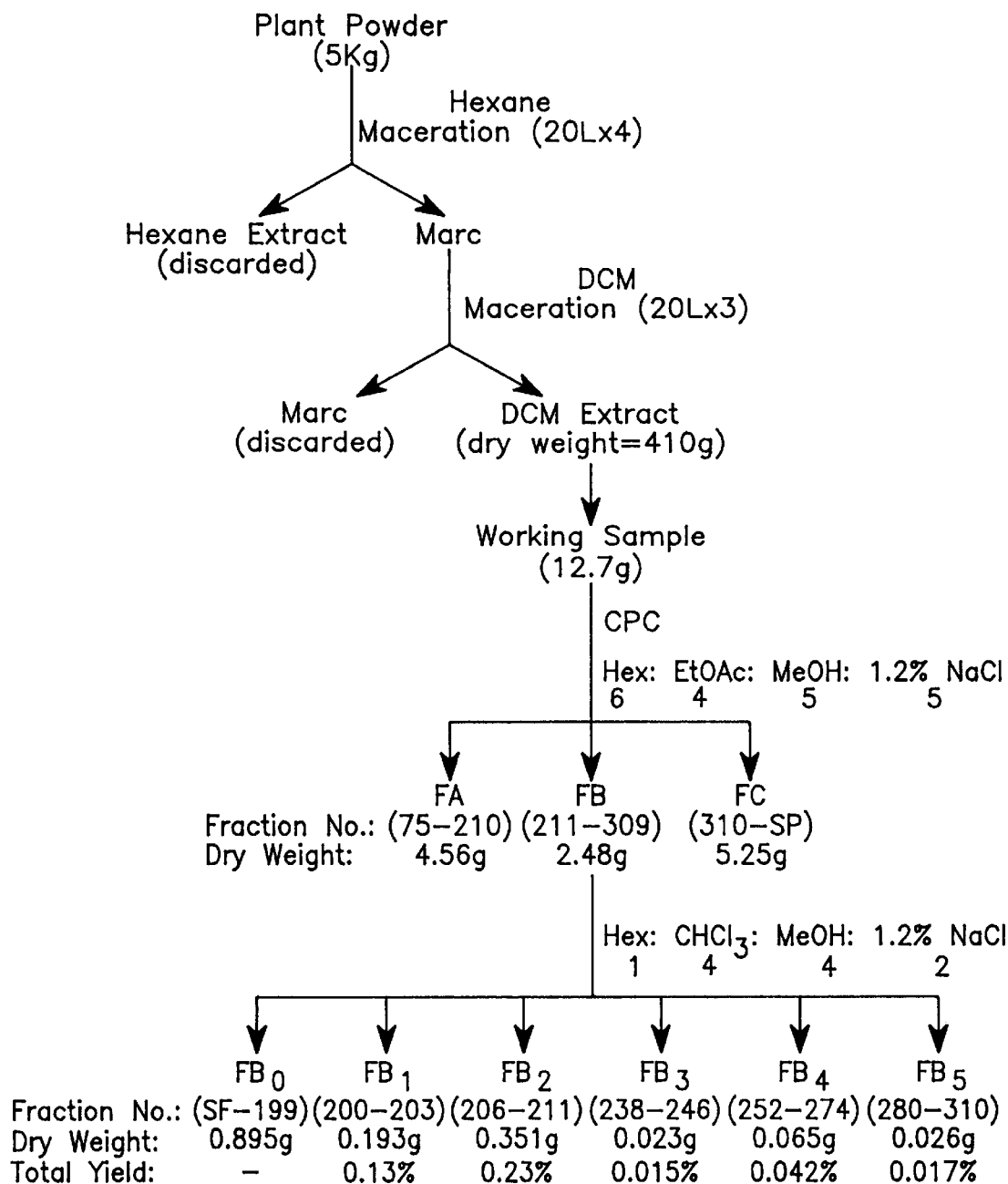

FIG. 5 illustrates a large scale, differential fractionation and CCC purification of lignans from the creosote bush, L. tridentata.

Figure 6A:
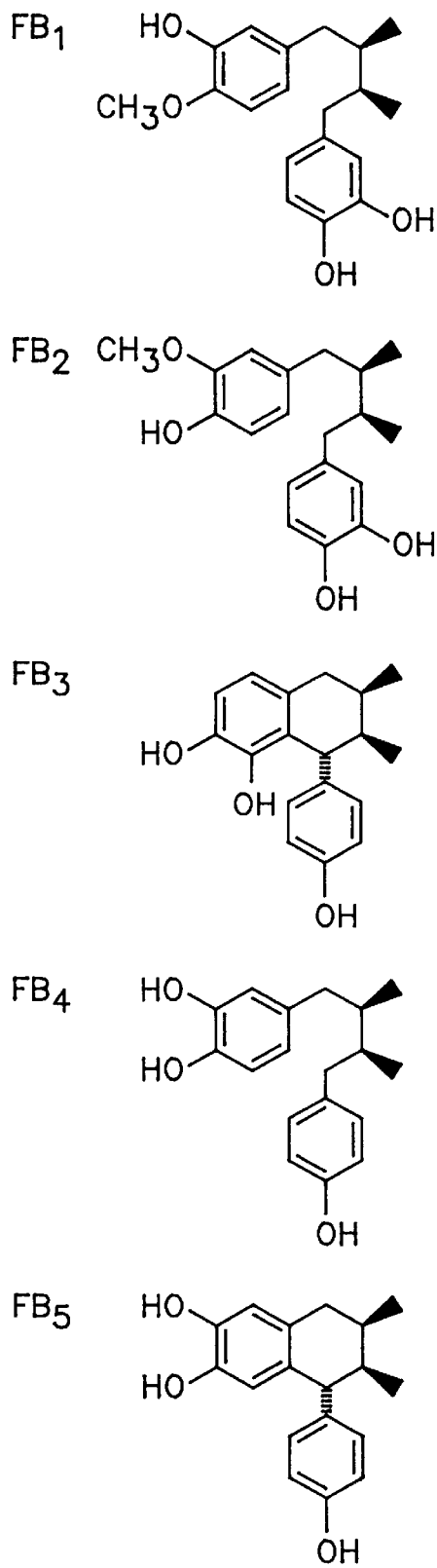
Figure 6B:
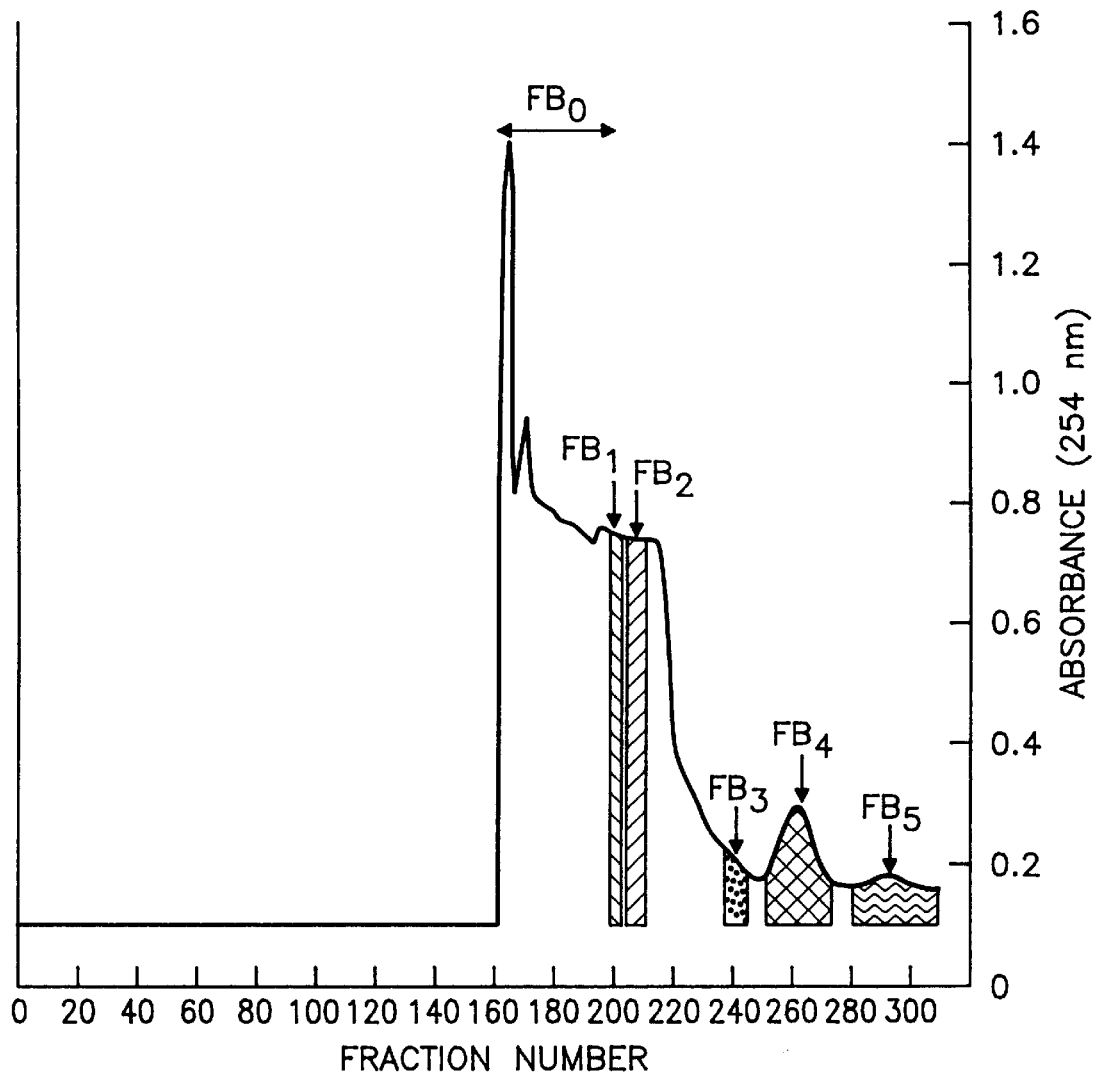

FIGS. 6A–6B show the CCC chromatogram of the large scale isolation of creosote bush lignans described in FIG. 5. The cyclolignans FB$_3$ and FB$_5$, which are among the compounds called "Rev.10:7," were also purified to nearly 100% purity in this CCC run.

Figure 7:
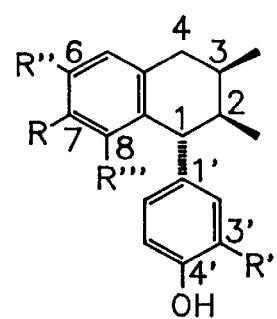

FIG. 7 shows the general chemical structure of cyclolignans identified or isolated from the creosote bush. Specific compounds are: table: 3'-demethoxyisoguaiacin; R is OMe, R' is H, R" is OH, and R'" is H; norisoguaiacin, R is OH, R' is OMe, R" is OH, and R'" is H; 3'-demethoxy-6-O-demethoxylisoguaiacin (FB$_5$), R is OH, R' is H, R" is OH, and R'" is H; 3'-demethoxy-6-dehydroxy-8-O-demethoxylisoguaiacin (FB$_3$), R is OH, R' is H, R" is H, and R'"is OH; 6,3'-di-O-demethylisoguaiacin R is OH, R' is OH, R" is OH, and R'" is H.

Figure 8A:
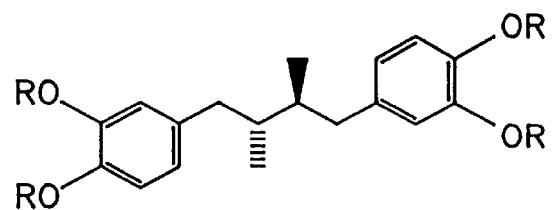
Figure 8B:
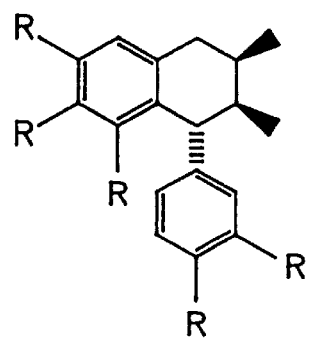
Figure 8C:
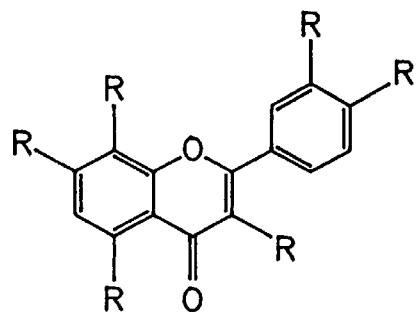

FIGS. 8A–8C show the general structures of the lignans and flavones isolated from extracts of the present invention. FIG. 8A shows the type 1 (bicyclic) lignans. These compounds are the subject matter of the related application U.S. Ser. No. 08/316,341. FIG. 8B shows the structure of the type 2 (tricyclic) lignans (cf. FIG. 7B). FIG. 8C shows the formula of the tricyclic flavones.

Figure 9:
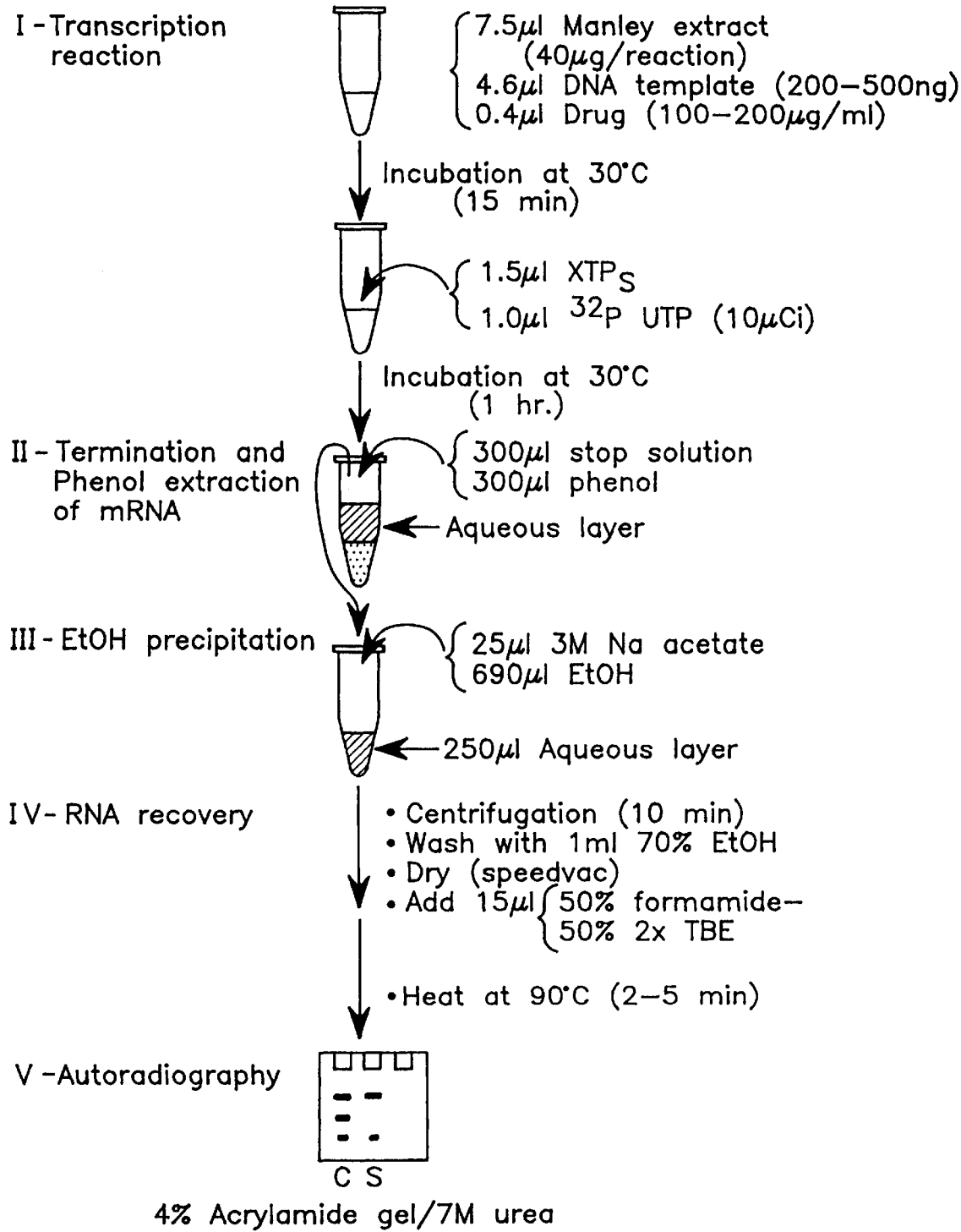

FIG. 9 shows a schematic diagram of the HIV gene transcription assay in vitro. This procedure was utilized to test lignans from the creosote bush including Rev.10:7 lignans (FB$_3$ and FB$_5$).

Figure 10:
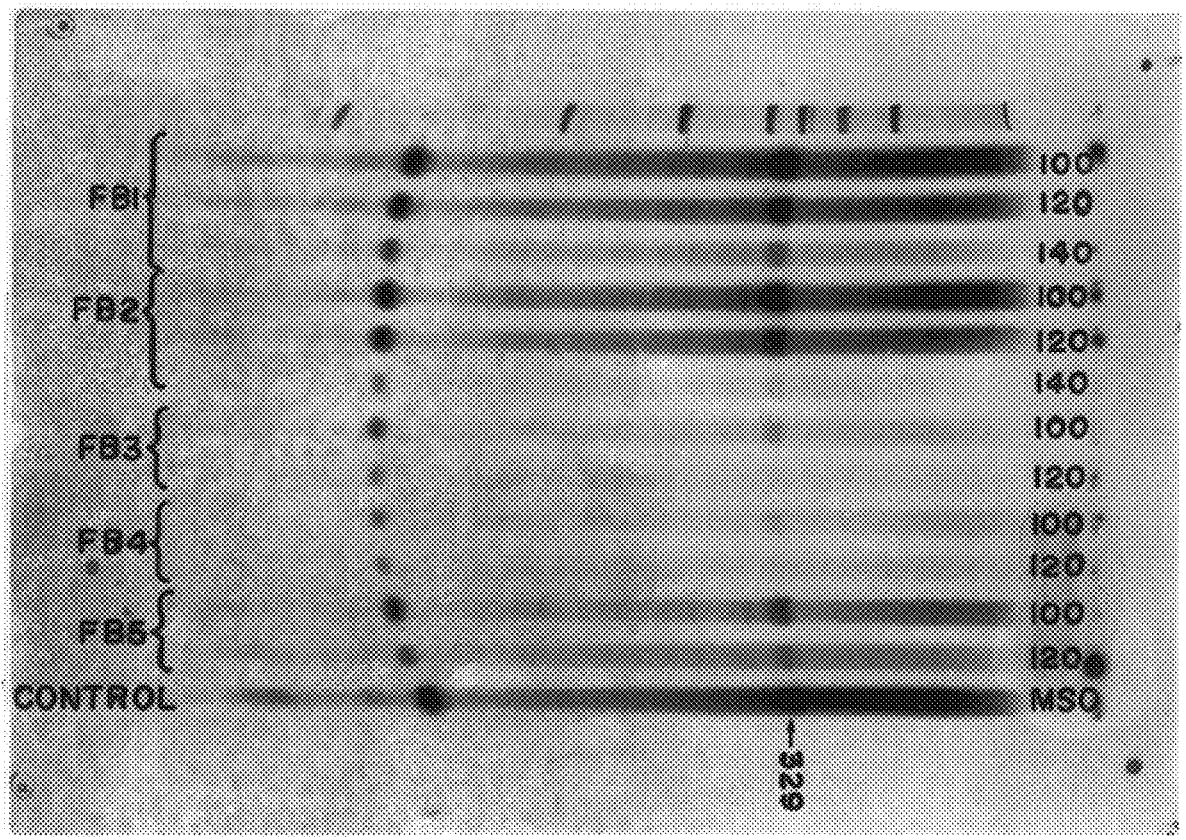

FIG. 10 shows the results of an in vitro gene transcription inhibition assay as described in FIG. 9. The inhibitory activity of the lignans prepared by the large scale isolation described in FIG. 6 is shown. The activity of the cyclolignans FB$_3$ and FB$_5$ is highlighted. Compounds FB$_1$, FB$_2$ and FB$_4$ were each tested at 100, 120, 140 μg/ml. Rev.10:7 lignans (FB$_3$ and FB$_5$) were tested only at 100, 120 μg/ml.

Figure 11:
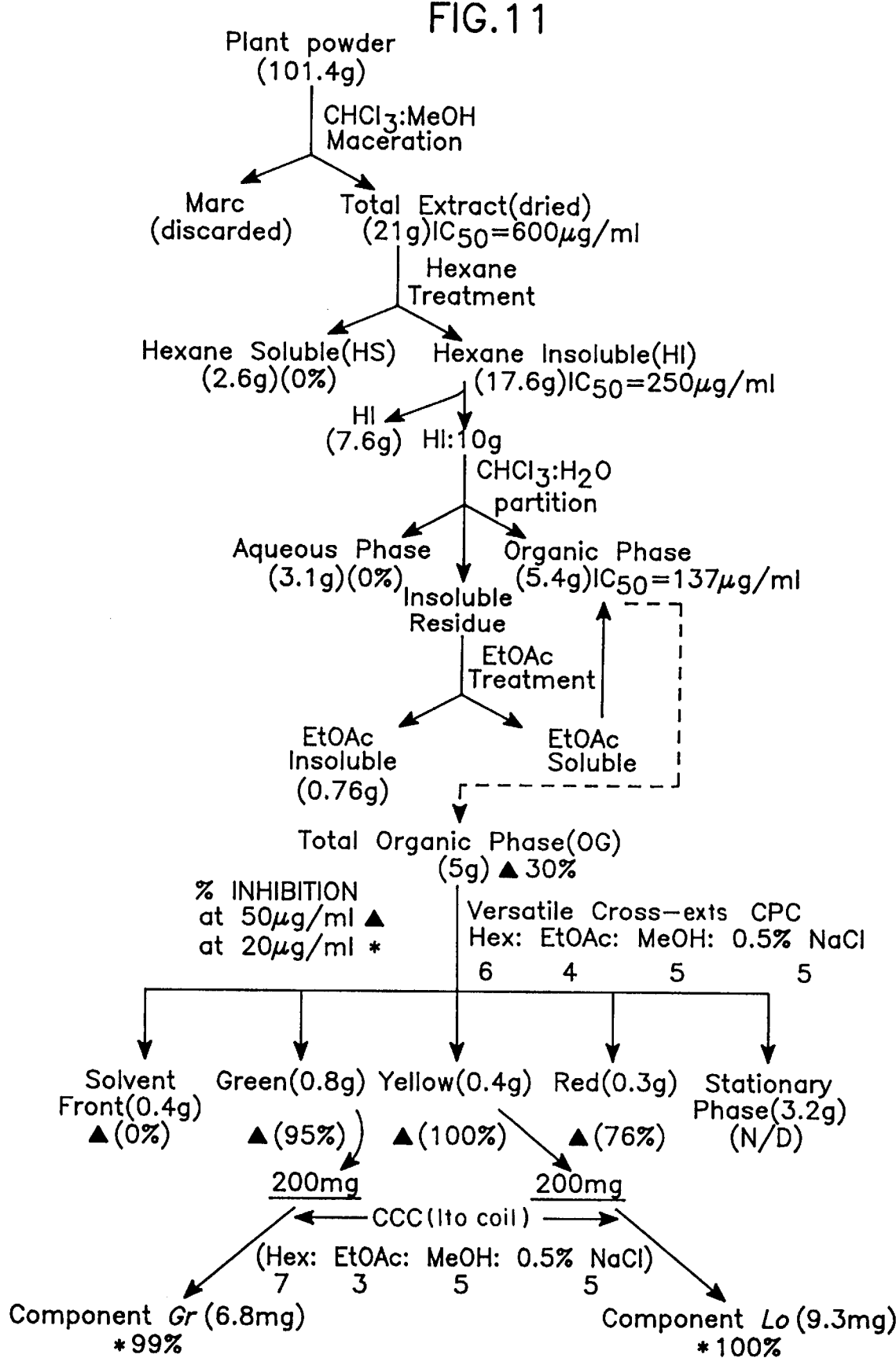

FIG. 11 shows an alternative extraction method which results in components Gr and Lo. Plant extracts were tested at each step for inhibition of HIV Tat-transactivation using the SEAP assay. Results of the assay are shown in parenthesis. SEAP assays were performed at 50 μg/ml (▲) or at 20 μg/ml (*).

Figure 12:
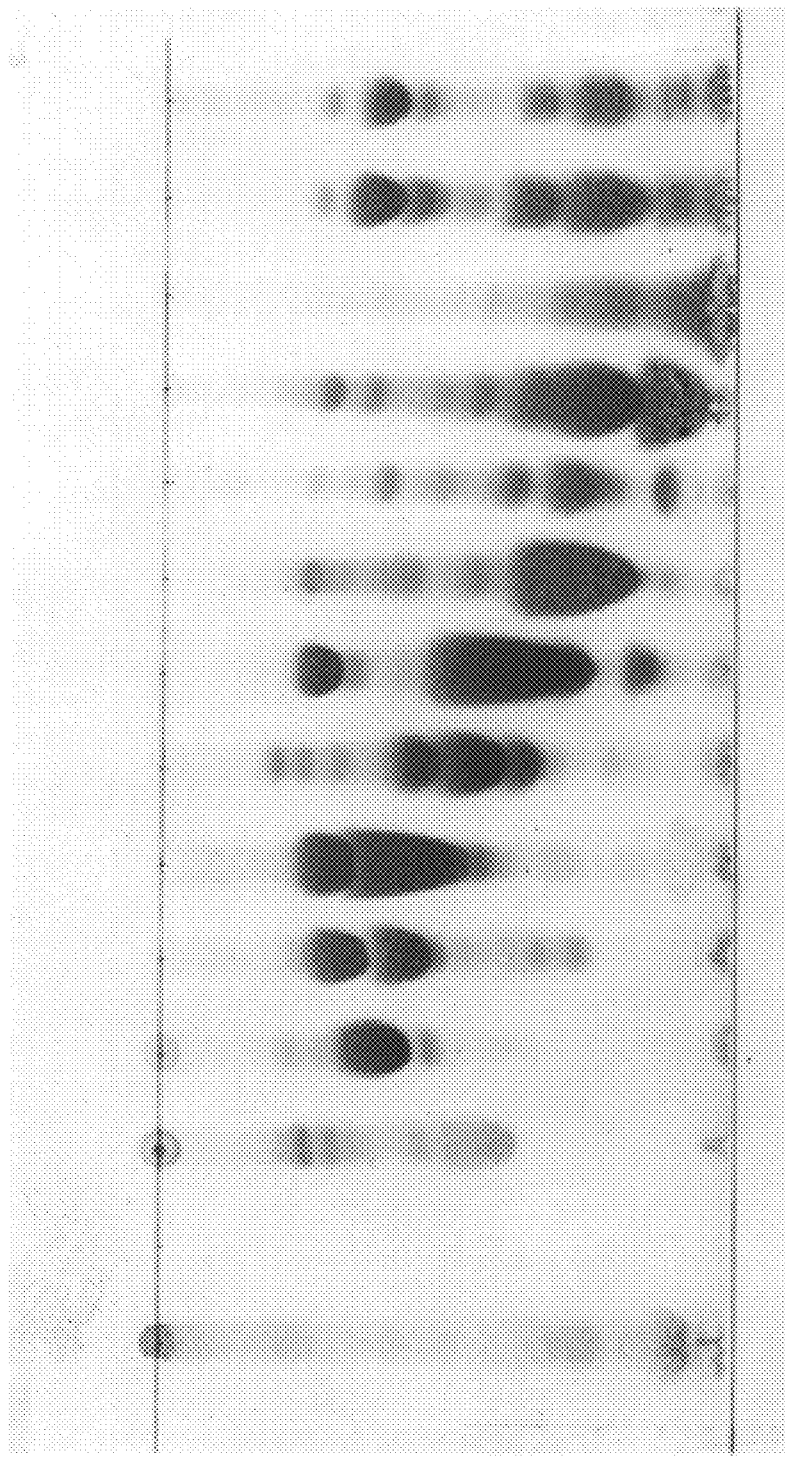

FIG. 12 shows a thin layer chromatogram of various extracts and compounds. 100 μg of each extract was spotted on a TLC plate (Whatman, Cat. No. 4420222); the chromatogram was developed in $CHCL_3$:MeOH:$H_2O$, 90:15:10. CBL=methylene chloride extract of *L. tridentata* leaves; 3-Magi=3-Magi extract of *Larrea tridentata*; A–J are the respective fractions of 3-Magi shown in the chromatogram of FIG. 3. The plate was developed by charring with 2% (w/v) $CeSO_4$ in 5.6% (v/v) $H_2SO_4$.

Figure 13:
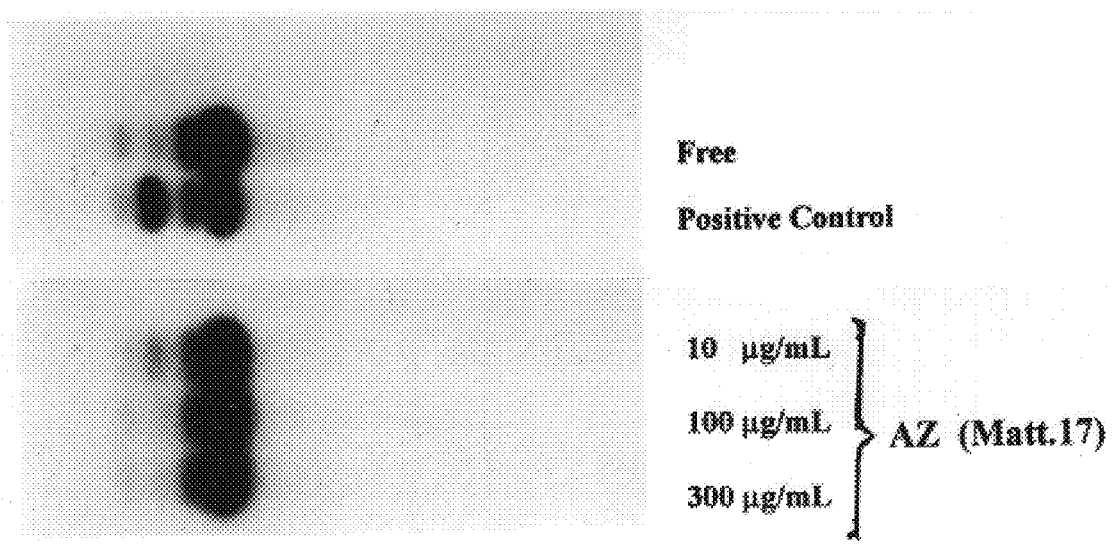

FIG. 13 shows the results of assays of HIV-1 integrase inhibition activity of an extract prepared from *Ambrosia deltoida*. Free=substrates only (no test compound, no integrase); Pos. Ctrl.=positive control (substrates plus integrase, no test compound).

DETAILED DESCRIPTION OF THE INVENTION

The present invention resides partly in extracts and cyclolignans purified from the leaves and flowers of the creosote bush (*Larrea tridentata*, Zygophyllaceae). The extracts and compounds have anti-HIV activity. The extracts, especially of *L. tridentata*, can be made by either of two methods, shown in flow-chart form in FIGS. 5 and 10.

The purified cyclolignans of the 3-magi extract, named "Rev.10:7" as a class, can be prepared by counter-current chromatography (see e.g., FIGS. 6A and 6B). The purified compounds were characterized by GC-Mass spectroscopy and NMR and their chemical structures are shown in FIG. 7. The anti-HIV activity of these compounds, assayed by methods described above, include the following:

a) Rev.10:7 compounds suppress Tat-regulated as well as Tat-insensitive transactivation in retroviruses, especially lentiviruses, including the Human Immunodeficiency Virus (HIV);

b) Rev.10:7 compounds inhibit HIV gene transcription in vitro.

The early steps of the extraction process can be varied substantially. For example, the ratio of chloroform to methanol in the initial extraction step can vary from 1:10 to 10:1, but is preferably 2:1 to 1:2, most preferably 1:1.

"Green" and "yellow" fractions as described herein are identified by their color. The color fractions are identified by analyzing counter-current chromatography fractions by thin layer chromatography and noting the color of the resultant components. Component Gr of the green fraction is the green component of the green fraction that is present in greatest amount. Similarly, component Lo is the major yellow component of the yellow fraction.

Also, the later steps of the purification are somewhat variable. For example, in the counter-current chromatography steps, the amount of salt in the solvent can range from 0.2% to 2%, preferably being between 0.5% to 1.5%. Most preferably, the amount of salt in the solvent is 0.5% to 1.2%. For example in the CCC fractionation of the "total organic phase" extract the amount of NaCl used was 0.5%. On the other hand, in the CCC fractionation of the "DCM extract" (FIG. 5), the amount of NaCl used was 1.2%. However, the ratios of the various components of the counter-current chromatography solvents are variable only within certain ranges if one expects to obtain fractions having the compositions identified herein. Large differences in the solvent compositions are expected to result in inadequate separation of the various components. However, the solvent compositions can be changed so long as fractions containing tricyclic compounds, and most desirably the O-lower alkyl derivatives of the tricyclics, are obtained. O-lower alkyl derivatives of tricyclics according to the present invention are preferably O-methyl, O-ethyl, or O-propyl derivatives. From 0 to 9 positions of the aromatic rings of the tricyclics can be O-alkylated, with 1–6 positions O-alkylated being preferred and 1–3 positions O-alkylated being most preferred.

Additional hydroxyls can be added to tricyclics already bearing a hydroxyl using tyrosinase. Alternatively, para-hydroxylation can be accomplished by nitration, followed by reduction to an amine, in turn followed by treatment with concentrated nitrous acid and subsequent dilution into warm water. Extant hydroxyls on the rings can be alkylated by the typical reactions. For example, Gisvolde et al. (O. Gisvolde and E. Thaker, *J. Pharmaceutical Sciences* 63:1905–1908 (1974)) describe methylation to the methyl ether using potassium carbonate and dimethyl sulfate. As to the preparation of the ester compounds of the invention, esterification of hydroxyls is of course well-known in the art.

For performing the counter-current chromatography steps, the solvent from preceding steps is usually removed from the sample. The residue is then dissolved in the solvent used for the counter-current chromatography and then injected into the chromatograph.

The extract can be used at various stages of refinement, including complete purification of the active components and subsequent recombination of them. As compositions, preferable extract fractions are the fraction green, component Gr, fraction FA, fraction FB, and fractions $FB_3$, a mixture of fractions $FB_3$ and $FB_5$, and mixtures of either of $FB_3$ or $FB_5$ together with any or all of $FB_1$, $FB_2$ and $FB_4$. An especially preferred fraction comprises components A–J shown in FIG. 3. Preferable fractions for use in treatment of viral infections are all of the above-noted fractions and also fraction $FB_5$.

Figure 3:
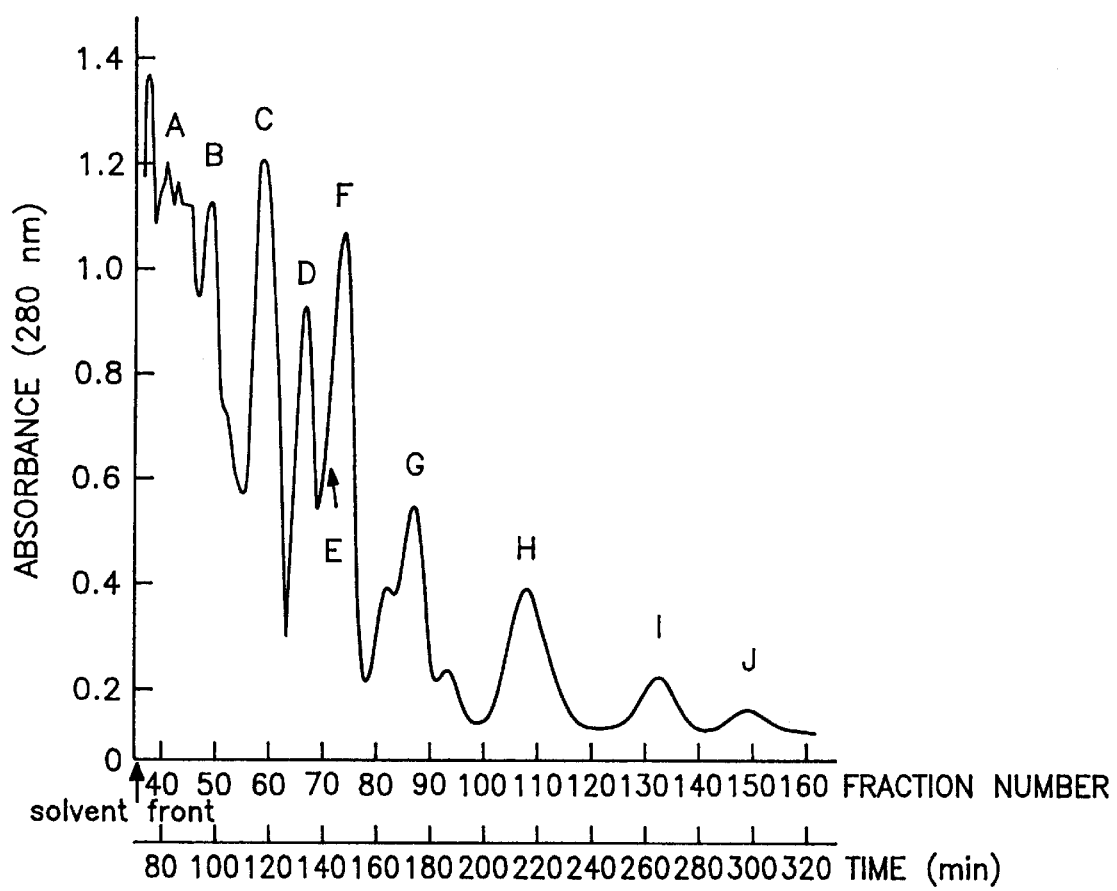
FIG. 3 shows the results of countercurrent chromatography (CCC) of 3-Magi extract. The chromatogram of a run using 58 mg 3-Magi using Hex:CHCl$_3$:MeOH:0.2 M NaCl at 1:2:2:4 ratio as the solvent is shown. Fractions B and D can be obtained at >90% purity in a single run under these conditions. 3-Magi extract is defined as the relatively nonpolar compounds from the CCC fractionation encompassing fraction #39 to 160. This corresponds to peak A to J on the CCC chromatogram in FIG. 3A. Components A through J constitute the following fractions.

The fraction FA comprises principally a mixture of O-methyl derivatives of the tricyclic compounds of the invention. The peak A of the chromatogram shown in FIG. 3 is similarly comprised of O-methyl derivatives of the tricyclic compounds of the invention.

It is known that $FB_3$ and $FB_5$ are trihydroxy derivatives of tricyclics (see, FIGS. 6A and 6B). Methylation of $FB_3$ and $FB_5$ greatly increases their Tat transcription inhibitory activity and their HIV replication inhibitory activity (see, Table 1). Especially preferred compounds of the invention are the tricyclic lignan shown as compound $FB_3$ shown in FIG. 6A and its O-methyl derivatives.

Referring to the general formula (I), preferred purified compounds of the invention are those wherein a plurality of $R^1$ to $R^9$ are $CH_3O$—, more preferable compounds are those wherein 6 or fewer of $R^1$ to $R^9$ are $CH_3O$—, most preferable compounds are those wherein 3 or fewer of $R^1$ to $R^9$ are $CH_3O$—.

The present invention also encompasses extracts prepared from the common weed *Ambrosia deltoidea*. Such extracts are shown to be active as inhibitors of Tat transactivation and also as inhibitors of HIV-1 integrase.

The present invention encompasses extracts prepared from the creosote bush *Larrea tridentata*, or other plants which contain the active compounds described herein. The present invention also encompasses methods for the treatment of retroviral or lentivirus infection, including HIV infection, by administration of a viral replication-inhibiting amount of the extract to a patient infected with a lentivirus or other retrovirus. Without being bound by any theory of the invention, the present Inventor has shown that the purified cyclolignans of the invention inhibit binding of Sp1 protein to enhancer sequences in the HIV-LTR promoter of HIV. As described elsewhere in the specification, in HIV the inhibition of Sp1 binding to the LTR has the effect of suppressing proviral transcription, blocking Tat-transactivation and inhibiting viral replication. Thus, in addition to being used for treating lentivirus infection, the extracts of the invention can be used to treat infections by other viruses whose replication is dependent upon binding of Sp1 protein to a viral promoter.

It should be clear from the above hypothesized mechanism that the extracts and cyclolignans of the invention can be used in vitro as reagents for inhibiting binding of Sp1 to viral promoter sequences.

The extract of the present invention contains a mixture of related polycyclic lipophilic compounds, especially bicyclic and tricyclic lignans. Also present in the mixture are a number of fatty acids. Accordingly, formulations of the extract for pharmaceutical use can be prepared by methods typical in the art for lipophilic compounds. See e.g., *Remington: The Science and Practice of Pharmacy*, 19th ed., esp., Chapters 83–95, c. 1995 by Mack Publishing Co., Easton, Pa.

Oral administration of the extracts is preferred. Accordingly, the extracts will preferably be prepared as capsules, tablets or syrups. Due to the lipophilic nature of the active components of the extract, transdermal administration via "patch" applications is also a useful route of administration. However, other routes of administration, such as i.v., i.p., i.m. are also expected to be effective.

An effective anti-viral dose is expected to require adjustment for the particular virus encountered. The required dosage can be determined by well-known methods based upon in vitro tests of anti-viral activity and data as to bioavailability and distribution of the active compounds obtained by standard experiments. Formulations providing unit doses of 1 to 1000 mg dry weight of the extract are expected to provide an effective anti-viral amount of the extract to a 50 kilogram individual. Preferably, formulations will provide unit doses of 1 to 200 mg, more preferably 1 to 25 mg, most preferably 5 to 20 mg of the extract.

Unit doses are administered over periods ranging from twice per day to one dose per two weeks, preferably once per day or once every other day.

In the case of continuous administration via patch or other method, a formulation will provide a plasma concentration of the components totalling 0.01 $\mu$g/ml to 10.0 $\mu$g/ml, preferably ranging from 0.1 $\mu$g/ml to 5.0 $\mu$g/ml, most preferably from 1.0 $\mu$g/ml to 5 $\mu$g/ml. When the extracts Gr or 3-Magi are administered, it is preferred that the amounts of individual components A–J of the extract reach plasma concentrations according to their proportions shown in FIG. 3. On the other hand, where the more refined extract FB is administered, the amounts of the individual components $FB_1$, $FB_2$, $FB_3$, $FB_4$ and $FB_5$ are preferably distributed in proportion to their amounts (as dry weight) shown in FIG. 5. Where the individual fractions $FB_3$ or $FB_5$ are administered, the preferred range of plasma concentration is 5 $\mu$g/ml to 50 $\mu$g/ml, more preferably 10 to 30 $\mu$g/ml.

The currently FDA-approved drug regimen for treatment of HIV involves a combination of inhibitors of reverse transcriptase (AZT, ddI, 3TC) and protease inhibitors. Although promising, this drug regimen has already been shown susceptible to the development of viral resistance since the drugs are targeted at gene products (proteins and enzymes) which are subject to variation in molecular structure. In contrast, 3-Magi inhibits gene transcription and suppresses the replication of all multidrug resistant HIV mutant strains. Furthermore, this extract suppresses Tat-regulated transactivation as well as Tat-insensitive gene transcription. An integrase enzyme appears to be a component conserved among most, if not all, retroviruses.

When used in combination, dosage for 3-Magi extract will be 10, 30, 50 or 100 mg unit doses and is preferably administered orally, in the form of capsules, tablet or syrup. For each capsule/tablet, the proportion of 3-Magi can range from ½ to ¾ of the total concentration formulation is one having ⅔ 3-Magi. Unit doses can be administered according to the schedule described above.

The invention being thus described, the Examples following serve to illustrate specific embodiments of the invention. The following examples are illustrative only, and do not limit the scope of the invention, which rather is defined by the claims below.

The extracts of the invention are prepared by the following procedures. Biological activities of the extracts and purified cyclolignan compounds are shown by the assays described hereinbelow.

General Materials and Methods

Cell line. COS cells were maintained as previously described (Cullen, *Cell* 46:973–982, 1986).

Plasmid DNAS. DNA transfection of mammalian cells was performed using a modified procedure of the lipospermine method originally described elsewhere (Loeffler and Behr, *Methods in Enzymology*, 217:599–618, 1993). All plasmids were from Dr. Bryan Cullen, Duke Medical Center. Plasmids pSEAP and pBC12/CMV and HIV LTR and Tat DNA are commercially available from Clontech and Stratagene. Plasmid transformation was into the *E. coli* MC1061 strain, which was obtained from Dr. Barbara Bachmann, Department of Biology, Yale University. The *E. coli* MC1061 strain can also be purchased from Clontech. Plasmid DNAs were purified using a QIAGEN® purification kit (Qiagen).

Chemical Reagents. Diethanolamine (cat. #31S89) and pnitrophenylphosphate (cat. #71768) were purchased from Fluka BioChemika, and L-homoarginine (cat. #H-1007) was purchased from Sigma Co. TRANSFECTAM® (Promega #E123A) was used as the lipospermine reagent in DNA transfection studies.

The SEAP Assay. The "SEcreted Alkaline Phosphatase" assay for Tat transactivation has been described previously (Berger et al., *Gene* 66:1–10, 1988; Bohan et al., *Gene Expression* 2(4):391–407, 1992). The details of the entire procedure for the SEAP inhibition assay as used herein have been described (Gnabre et al. *Journal of Chromatography A* 719:353–364 (1996)).

The secreted alkaline phosphatase analysis was performed as originally described by Berger et al. In this assay, a DNA expression vector wherein a structural gene encoding a secreted alkaline phosphatase is driven by an enhancer-linked promoter is transfected into target cells. The cells are then exposed to compounds which affect the binding/activation of the transcription regulatory proteins, and the amount of SEAP activity in the medium is measured.

As to the alkaline phosphatase assay, briefly, a 250-$\mu$l aliquot was removed from COS cell culture supernatants, heated at 65° C. for 5 minutes to selectively inactivate endogenous phosphatase (SEAP is heat stable) and centrifuged in a microfuge for 2 minutes. One hundred pl of 2×SEAP assay buffer (1.0 M diethanolamine, pH 9.8; 0.5 mM MgCl$_2$; 10 mM L-homoarginine) was added to 100-μl aliquot of the samples. The solution was mixed and transferred into a 96-well flat-bottom culture dish (Corning). Twenty μl of pre-warmed substrate solution (120 mM p-nitrophenylphosphate dissolved in 1×SEAP assay buffer) were dispensed with a multipipeter into each well containing the reaction mixture. The A$_{405}$ of the reaction was read at 5-minute intervals at 37° C. for 60 minutes using an EL340i microplate reader (Bio-tek Instruments, Inc.) with 5-second automatic shakings before each reading. The change in absorbance was plotted against time in the standard assay of SEAP induction. In the drug screening assay, the percent inhibition of SEAP expression was calculated at its 30 min endpoint as follows:

$$\% \text{ Inhibition}=100-[(CT^+-C^+)/(CT^--C^-)]\times 100$$

Where:

C$^-$: Control sample (no DNA, no drug)

CT$^-$: Control sample (+DNA, no drug)

C$^+$: Drug-treated sample (no DNA, +drug)

CT$^+$: Drug-treated sample (+DNA, +drug)

EXAMPLE 1

Preparation of the Semi-purified 3-Magi Extract by Counter-Current Chromatography (CCC)

The leaves and flowers of the creosote bush *Larrea tridentata* were collected from southwest Arizona, based on ethnopharmacological inquiries (see, P. C. Standley, in "United States National Museum: Plants and Shrubs of Mexico," Vol. 23, pp. 521, P. C. Standley, ed., c. 1961 by the Smithsonian Institution, Washington, D.C.; C. W. Waller and O. Gisvolde, *J. Am. Pharm. Assoc.*, 34:78 (1945).). Plant materials were dried and ground in a 3 mm screen Willy mill. The plant powder (5 kg) was treated with hexane by successive macerations. The soluble fraction of the hexane extract was discared and the marc was dried and extracted with methylene chloride (dichloromethane, DCM) by successive macerations. The DCM extract was dried to residue. This generated 410 g of crude extract.

The preparation of 3-Magi extract was achieved by CCC fractionation of the DCM crude extract as follows.

A working sample of 50 mg extract was fractionated by counter-current liquid-liquid partition chromatography using the previously described triplet coil planet centrifuge ("CPC," Ito et al., *J. Liq. Chromatogr.*, 13:2329–2349, 1990). The optimal solvent system was a mixture of hexane:EtOAC:MeOH:1.2% NaCl, in the ratio of 6:4:5:5, with the upper phase (organic layer) as the mobile phase. The entire 50 mg of DCM extract was dissolved in 6 ml of a mixture of the two phases and introduced into the coil via a syringe. The mobile phase was pumped through the coil while rotating it at 1000 rpm. At a flow rate of approximately 1 ml per minute, approximately 40% of the stationary phase was initially lost (60% retention). After the appearance of mobile phase in the eluate (34th tube), fractions of mobile phase were collected, evaporated to dryness, monitored by TLC and pooled, according to Rf and color of spots following cerium sulfate charring, into several batches (FIG. 3). The chemical composition of each batch was determined by GC-Mass Spectroscopy and NMR (see, FIGS. 4A–4G).

To obtain the semi-purified 3-Magi extract, fractions #34–38, which contain cytotoxic volatile constituents and essential oils, were discarded. Fractions #39–160 corresponding to peaks A to J in FIG. 3 were pooled and saved. This semi-purified fraction was denoted, "3-Magi Extract" or "3-Magi", and was utilized in biological activity assays after additional treatments described in Example 3.

EXAMPLE 2

Preparation of Extracts Containing the Component Gr

Assay-Guided Fractionation of the First Batch of Plant Materials, a Pilot Study

Figure 1A:
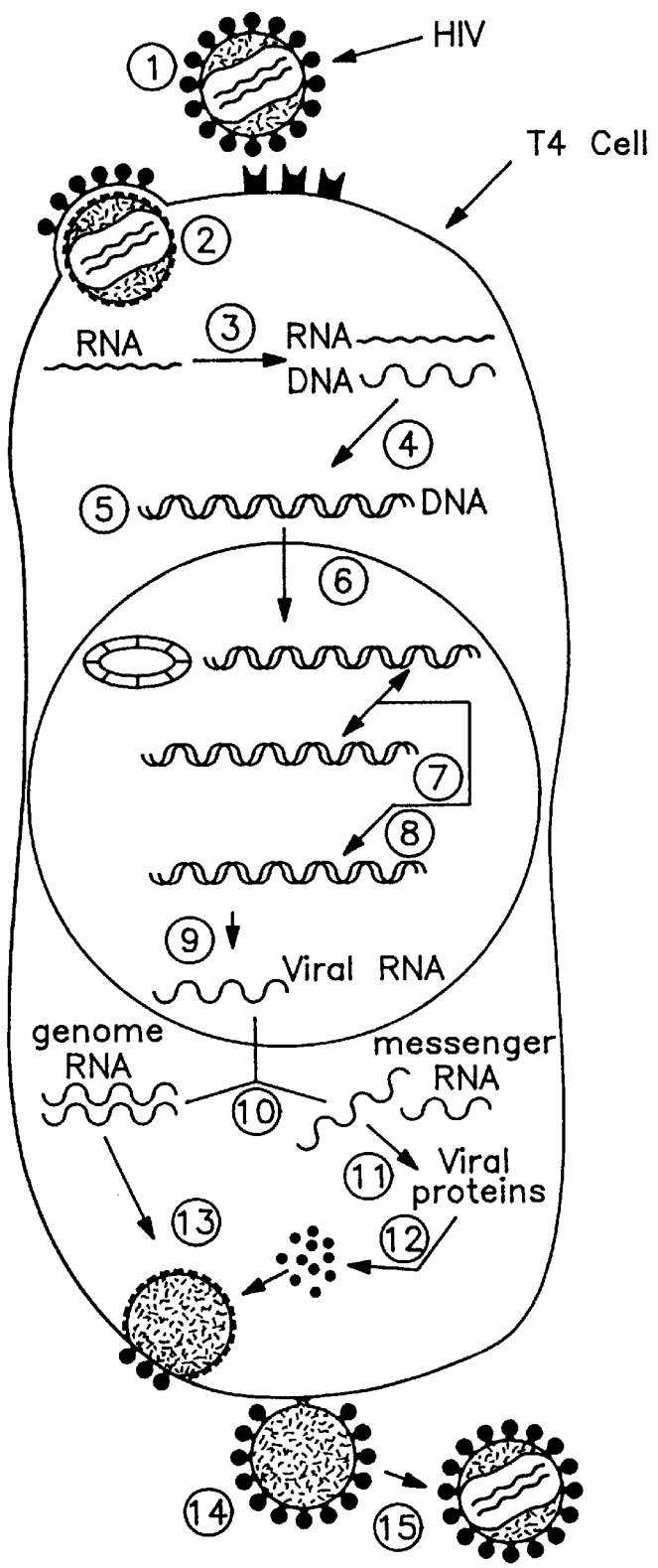
FIGS. 1A and 1B graphically illustrate the life cycle of HIV-1.
Figure 1B:
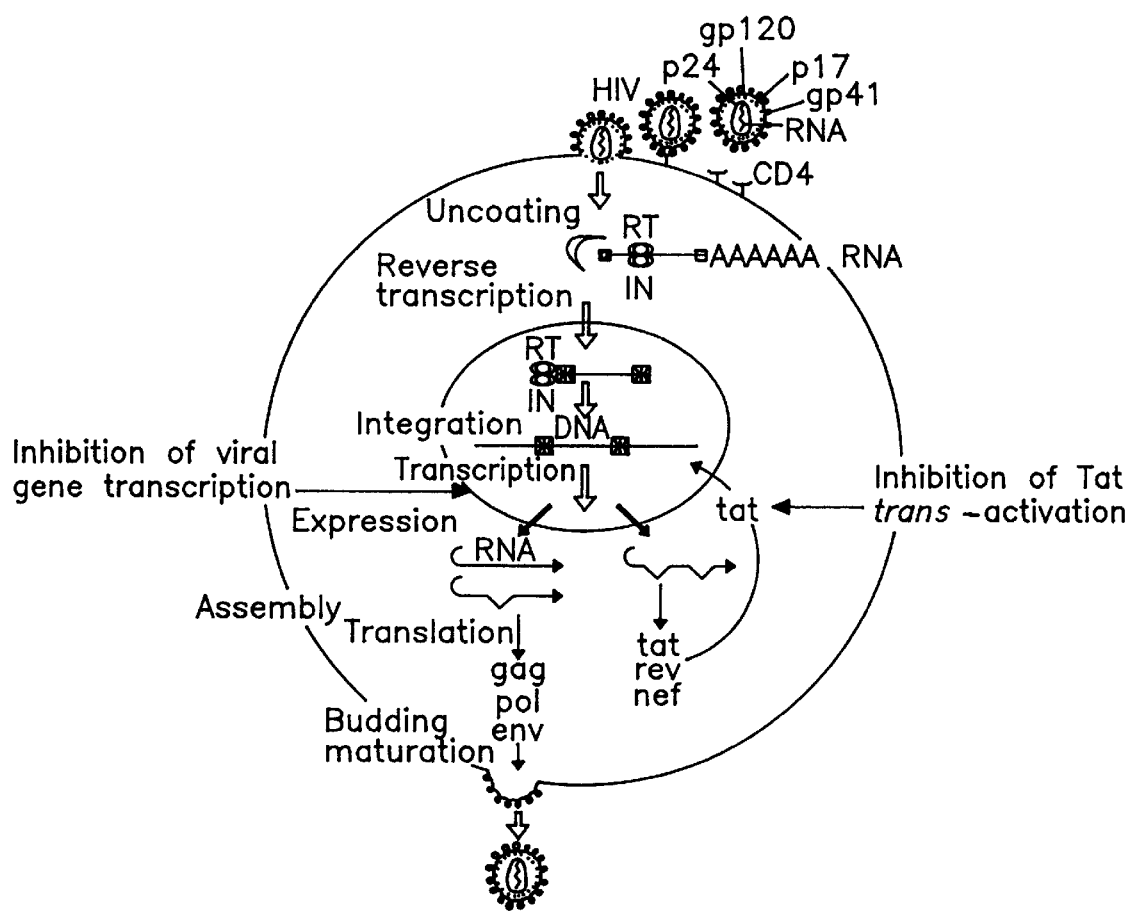
Figure 2:
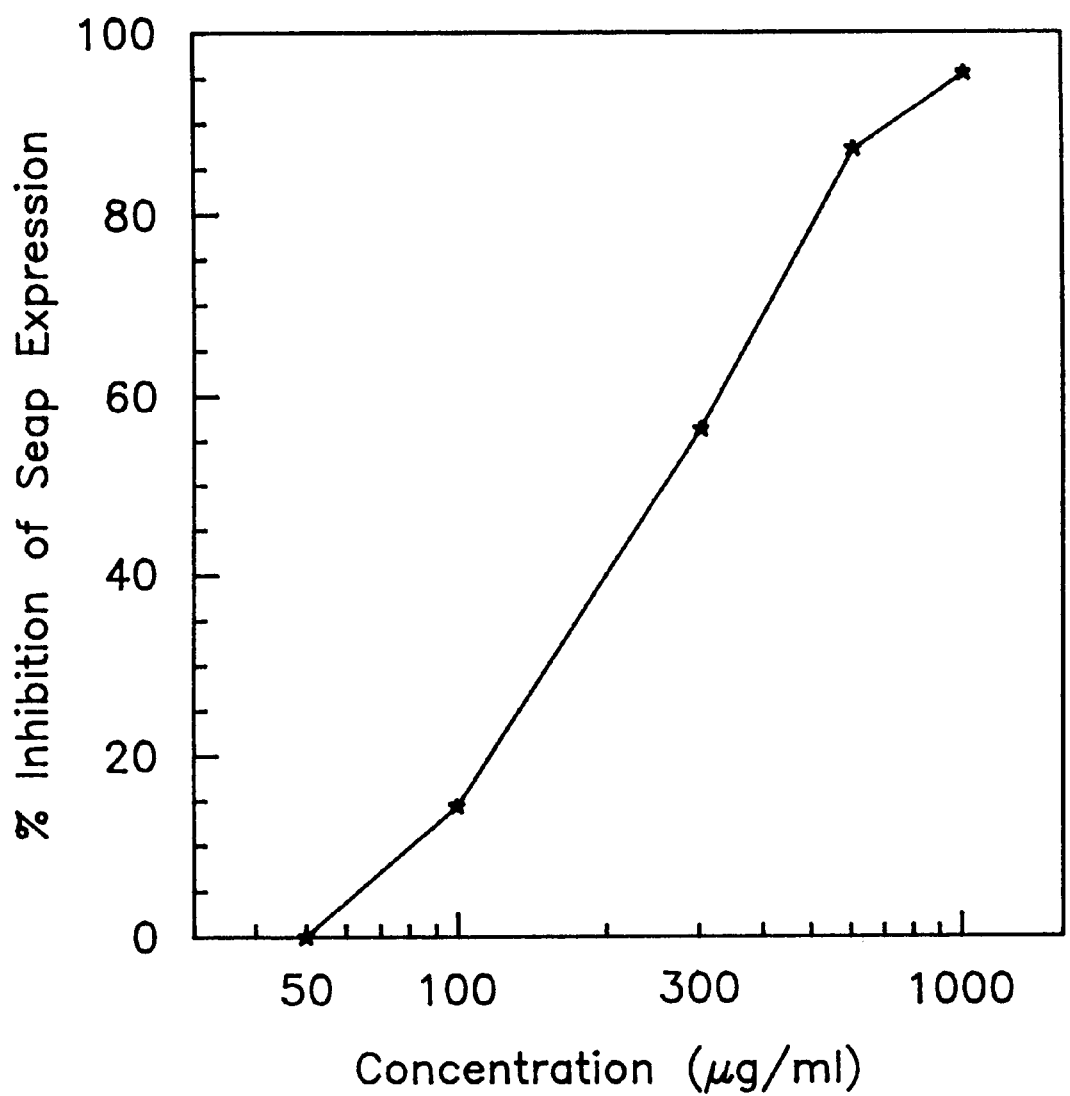
FIG. 2 shows the inhibition of Tat-TRS activity by the hexane insoluble fraction 3-Magi extract in the secreted alkaline phosphatase (SEAP) assay. Triplicate samples of COS cells were transfected with a mixture of pBC12/HIV/SEAP and pBC12/CMV/t2 (encoding Tat) in a 2:1 ratio, using the lipospermine procedure (J. P. Loeffler and J. P. Behr, Meth. Enzymol. 217:599 (1993)). Cells were incubated for 12–15 hours after transfection before the extract was added at the various concentrations noted. The cultures were incubated for 48 hours, after which 250 μl of the culture supernatant was assayed for SEAP activity as described in Example 4. Each data point represents the average of nine determinations.

In a pilot study, the fractionation of plant materials (101.4 g) started with successive macerations of the powder using a mixture of chloroform-methanol. This total extract was tested in the SEAP assay and displayed a dose-dependent inhibitory activity of Tat transactivation with an IC$_{50}$≈600 μg/ml (the IC$_{50}$ is the concentration exhibiting 50% inhibitory activity, and is a measure of drug potency; see FIG. 2). The same extract was also found to inhibit HIV replication and protect the human lymphoblast CEM-SS cells against HIV-induced cell death in the formazan assay (J. N. Gnabre et al., submitted to Proc. Natl. Acad. Sci. 1996; M. A. Weinhold et al., *J. Natl. Cancer Inst.* 81:557 (1989)). However, this extract exhibited a narrow range of activity and a marked intrinsic cytotoxicity. Based on these test results, the total extract was defatted with hexane to remove fats, waxes, and volatile constituents potentially toxic to culture cells. The hexane-insoluble (HI) fraction was tested in the SEAP assay. The HI fraction shows a concentration-dependent activity with an IC$_{50}$=250 μg/ml.

A working sample of 10 g HI residue was subjected to differential fractionation by first partitioning in chloroform-water to generate three fractions: (1) an inactive aqueous phase residue; (2) an enriched chloroform phase; and (3) an insoluble residue. The latter residue was further treated with ethyl acetate (EtOAc), and yielded 0.76 g of EtOAc-insoluble materials and an EtOAc-soluble fraction. Based on the similarity of the TLC patterns, the EtOAc-soluble fraction was combined with the chloroform fraction, yielding 5.4 g of an active organic phase (OG) with IC$_{50}$=137 μg/ml. Thus, chloroform-water partition of the hexane-insoluble fraction generated an enriched organic phase with a four-fold increase in activity compared with the original total extract.

Isolation of the Anti-HIV Components (Gr and Lo) by Counter-Current Chromatography Further fractionation of the major components from the organic phase (OG) was achieved by counter-current chromatography (CCC) using the versatile cross-axis coil planet centrifuge (CPC) with a pair of multilayer coils mounted at the off-center position (K. Shinomiya et al., *J. Chromatogr.* 644:215 (993)). The solvent system was a mixture of hexane-EtOAc-methanol-0.5% NaCl in the 6:4:5:5 ratio, with the organic layer as the mobile phase. This solvent system was denoted the "hexane system." The ratio of this system was determined based on the values of the partition coefficient (K). Here, K was defined as the ratio of the activity of the component(s) in the aqueous phase over the actvity of the same component(s) in the organic phase. In the initial pilot studies, K values were primarily assessed by SEAP bioassay on a trial-and-error basis since the active components had not been identified. The above hexane system ratio provided a K value of 0.7, which was within the suitable range of a good CCC separation (D. G. Martin, p. 78 in *Modern Countercurrent Chromatography*, ACS Symp. Ser. No. 593, W. D. Conway and r. J. Petrosky, eds., 1995.)

Five grams of the OG fraction from the pilot studies was fractionated by CCC with the hexane system, with approximately 68% retention. The fractions were monitored by SiO$_2$ TLC using the analytical chloroform system, chloroform-methanol-water (lower phase) in 80:20:10 ratio, and pooled into five batches based on the similarity of TLC patterns. These batches included: solvent front, fraction green, fraction yellow, fraction red and stationary phase (SP). All these fractions were further SEAP-assayed at 50 μg/ml for inhibition of HIV Tat transactivation. The percent inhibition is given in parentheses in FIG. 11.

Further analysis of fractions green and yellow (95 and 100% activity, respectively) led to the identification of two major components of different $R_F$ values in the analytical chloroform system, i.e., chloroform-methanol-water (lower phase) in 80:20:10 ratio: (1) a $R_F$=0.8 component generated from fraction green, and (2) and a $R_F$=0.6 component from fraction yellow. These components were separately fractionated by CCC with the hexane system in 7:3:5:5 ratio using the highly efficient type-J coil planet centrifuge known as the Ito multilayer coil separator-extractor (N. B. Mandava and Y. Ito, p 823 in *Countercurrent Chromatography: Theory and Practice*, N. B. Mandava and Y. Ito, eds., c. 1988 by Marcel Dekker, New York, N.Y.). This solvent ratio gave a K value of approximately 1.5, which was determined by TLC analysis as the ratio of the concentration of the component of interest in the upper organic phase over the concentration of the same component in lower aqueous phase. From the initial 200 mg of fraction green, only 6.8 mg of clean $R_F$=0.8 component was recovered with ca. 80% purity. This constituted 0.05% yield based on the original weight of plant powder. The R=0.8 component was termed component Gr. Under similar conditions, 200 mg fraction yellow generated a widespread $R_F$=0.6 component whose elution peak tail afforded 9.3 mg of a fairly clean mixture, denoted component Lo (FIG. 11).

EXAMPLE 3

Preparation of Plant Testing Materials for Biological Assays

The 3-Magi extract was monitored by $SiO_2$ TLC with cerium sulfate charring, 2% $CeSO_4$ (w/V) in 5.6% $H_2SO_4$ (v/v), and by the SEAP assay for anti Tat-TRS activity. For the SEAP assay, test materials were dissolved in 10% DMSO solution made in calcium-free, magnesium-free PBS (Ca—Mg-free PBS). The suspension was centrifuged and the stock solution (10 mg/ml) was filter-sterilized using a Millex-GS 22 μm filter (Millipore). Appropriate dilutions of the stock solution were prepared in a final DMSO concentration of 0.2% in Ca—Mg-free PBS to obtain the various concentrations of test compounds.

EXAMPLE 4

Biological Activity of 3-Magi: Inhibition of Tat Transactivation in SEAP Assay

Suppression of viral gene transcription is an attractive target for anti-HIV drug development. Suppression of viral gene transcription appears to be a most promising approach in antiviral therapy since inhibition of viral transcription should in principle abolish the translation of all viral gene products such enzymes (protease, reverse transcriptases, integrase, etc.,) and specific regulatory proteins (Tat, Rev, Nef, etc.). Direct assay of in vitro transcription, aimed at identifying inhibitors of HIV gene transcription, is a screening tool which supplements the SEAP-based tissue culture Tat transactivation assay.

The SEAP in vitro assay for analysis of HIV-LTR-directed gene transcription has been reported. This assay served as a screening tool of several lignans extracted from the creosote bush, collectively termed "Rev.10:7," including the cyclolignans $FB_3$ and $FB_5$.

The 3-Magi extract prepared as in Examples 1 and 2 was assayed by the SEAP assay for anti Tat-TRS activity. The assay relies upon co-transfection of a plasmid encoding the HIV-1 Tat protein under the control of the CMV strong, constitutive promoter, together with a plasmid on which the SEAP gene is controlled by the HIV-1 LTR. Inhibition of Tat enhancement of LTR promoter activity is observed by measuring SEAP activity in the presence and absence of the compounds or extracts tested. Briefly, a day before DNA transfection, Linbro® 24 flat bottom wells of 17-mm diameter plates were pretreated with 0.5 ml sterile solution of 0.1% gelatin. The plates were kept in a tissue culture hood for 1 hour (all transfection steps were performed in the hood, unless otherwise stated). The gelatin solution was aspirated and the plates were washed with 0.5 ml of Iscove's Modified Delbecco's Medium (IMDM) supplemented with 10% fetal calf serum and antibiotics (complete medium). COS cells were seeded at a density of ≈$1.5 \times 10^5$ cells per 17-mm plate and incubated in a humidified 95% air/5% $CO_2$ incubator at 37° C. DNA transfection was performed at 50–60% cell confluency. The stock solution of the TRANSFECTAM reagent, DOGS, was prepared according to the manufacturer's advice at 1 mg/0.380 ml (2.38 mg/ml or 3.4 mM) in 10% (v/v) ethanol in distilled water. Ten minutes were allowed for the DNA-TRANSFECTAM interaction to proceed. Meanwhile, the growth medium was removed from the subconfluent COS cells and 300 μl (100 μl of complete IMDM+200 μl serum-free medium) were added to each well. The transfection cocktail was dispensed to the wells in equal volume. Control samples containing no DNA were similarly treated and received sterile 150 mM NaCl solution alone. All samples were incubated for 12 to 15 hours after which 700 μl of complete growth medium were added. The test compound (3-Magi extract) prepared in 5% DMSO/Ca—Mg-free PBS was immediately added at various concentrations to the wells. Control samples not treated with the 3-Magi extract received 5% DMSO/PBS solution alone (final DMSO concentration of 0.2%). All samples were then incubated for an additional 48 hours after which 250 μl of each culture supernatant was removed for SEAP analysis.

In the absence of any drug treatment, a nearly 65-fold increase in SEAP induction after 1 hour was observed, compared to the control (no DNA) assay or to the activity in cultures of cells transformed with the HIV-1 LTR/SEAP plasmid only. The inhibitory effect of the hexane insoluble fraction from which the 3-Magi extract is prepared is shown by the dose-response data in FIG. 2. The inhibitory effect of the component Gr, an extract prepared as shown in FIG. 11, is shown in Table 1.

TABLE 1

Inhibition of Tat-transactivation by an extract from *L. tridentata*

| Test Extract | Inhibition of Tat transactivation | |
|---|---|---|
| | 10 μg/ml | 20 μg/ml |
| Component Gr* | 73% | 100% |

*Component Gr is composed principally of tricyclic lignans having 1 or 2 methoxy groups on the rings.

Inhibition of HIV Cytopathic Effects

A compound inhibiting Tat transactivation should in principle block HIV replication. Consequently, component Green of 3-Magi extract was tested at the National Cancer Institute (NCI) for inhibition of HIV-1 cytopathic effects using the soluble-formazan assay (Weislow et al., *J. Natl.*

Cancer Inst. 81:577–586, (1989). In principle, CEM-SS cells (ATCC, Rockville, Md.) are cocultivated with HIV-producing H9 cells. Viruses infect the host CEM-SS cells, replicate and kill most of the CEM-SS cells in a week. If the drug inhibits HIV production, CEM-SS cells are protected from HIV-induced cell death. The tetrazolium (XTT) reagent is metabolically reduced by the viable cells to yield a colored formazan product which is measurable by colorimetry at 450 nm.

In practice, triplicate samples of CEM-SS cells (5000) were plated in 96-well microtiter plate. Appropriate concentrations of test compounds were added in a final volume of 100 μl calcium-magnesium-free PBS in 5% DMSO. Control samples received the compound medium alone. Five minutes later, 500 highly infectious HIV-1 producing H9 cells or normal H9 cells were added to the wells containing the appropriate drug concentrations. The microtiter plates were incubated at 37° C. in 95% air/5% $CO_2$ for 6 days after which a 50 μl mixture of XTT and N-methylphenazonium methosulfate (PMS) was added. The plates were reincubated for additional 4 hours for the color development (XTT formazan production). The plates were sealed, their contents were mixed by automatic shaking and the $A_{450}$ of samples was determined in a microplate reader. Each value represents the average of 3 determinations (Table 2). In presence of test compounds, no significant difference was found between the means of the duplicate values of the uninfected cells and HIV-challenged cells. In contrast, there was a significant difference ($p<0.05$) between HIV-challenged samples in the presence or absence of test compounds. The results of these studies are summarized in Table 2. At a concentration of 0.75 μg/ml for component Gr, there was an average 58% protection (cell viability) against HIV as opposed to 15% viability in drug-free samples challenged with HIV. Component Gr was devoid of cytotoxicity at the concentrations used.

TABLE 2

INHIBITION OF HIV-1 CYTOPATHIC EFFECTS BY CREOSOTE BUSH EXTRACT COMPOUNDS IN THE SOLUBLE-FORMAZAN ASSAY.

| Test Sample | Concentration of the test sample which yielded max protection against HIV without killing the cells μg/ml | Percent of live cells at day 6 as measured by XXT Formazan production | | |
|---|---|---|---|---|
| | | Uninfected plus test sample | HIV infected plus test sample | HIV infected minus test sample |
| Fraction Green | 0.187 | 59 | 67 | 16 |
| Component $G_r$ | 0.75 | 80 | 67 | 16 |
| Component $G_r$ (duplicate) | 0.75 | 70 | 48 | 14 |

EXAMPLE 5

Isolation and Characterization of the Cyclolignans, Rev.10:7

A large-scale isolation of anti-HIV-1 active constituents of the creosote bush was undertaken on five kg of plant powder treated with 20 liters of hexane 3 times. The hexane soluble fraction was discarded and the dry marc was extracted 3 times by successive macerations with 20 liters of dichloromethane (DCM). This afforded 410 g of DCM total extract (FIG. 5). A working sample of 12.7 g of this residue was initially fractionated by CCC on the large-capacity versatile cross-axis CPC (Shinomiya et al., J. Chromatogr. 644:215–229 (1993)) using the "hexane system" (hexane:EtOAc:MeOH: 1.2% NaCl) in 6:4:5:5 ratio with 1.2% NaCl in the stationary aqueous layer. The presence of salt in the aqueous phase significantly lowered the propensity for emulsification and improved the retention (70%) of the stationary phase. Using the upper phase (organic layer) as the mobile phase, 3 major fractions were identified (FIG. 5) based on the elution order and TLC patterns. These fractions included:

1) fraction FA (4.56 g) consisting of the early and most hydrophobic components;

2) fraction FB (2.48 g) enriched with the component of interest;

3) fraction FC (5.25 g) which consists of mostly polar components.

Further purification of fraction FB was achieved by CPC using the "chloroform system" (hexane:chloroform:methanol:1.2% NaCl) in 1:4:4:2 ratio, with the organic layer as a mobile phase. The sample was saturated with salt before injection. The presence of hexane in the chloroform system was required to account for the hydrophophilicity factor introduced by the salt, and to bring the partition coefficient into the 1–2 operating range. With 45% retention, this system permitted a remarkable resolution of most constituents ($FB_1$ to $FB_5$) of fraction FB, as illustrated in FIG. 6A. The structure of the compounds constituting $FB_1$ to $FB_5$ was determined by both GC-mass spectrometry and NMR. This study revealed that compounds $FB_1$ (0.193 g) and $FB_2$ (0.351 g) were isomers, derivatives of nordihydroguairetic acid (NDGA), namely, 4'-O-methyl-NDGA and 3'-O-methyl-NDGA, respectively. These two lignans occurred in 0.13% ($FB_1$) and 0.23% ($FB_2$) yield, based on the starting weight of plant powder. In contrast, their congener $FB_4$, which occurs in relatively lower yield (0.042%) appears to be a new lignan. Compounds of particular interest in this patent application are the cyclolignans $FB_5$ (FIG. 6A) also purified from this CCC run, and which occur in 0.015 and 0.017% yield, respectively. $FB_3$ has been described previously (Konno et al., J. Nat. Prod., 52:1113 (1989)), but $FB_3$ appears to be a novel compound. The compounds norisoguaiacin (FIG. 7) and 3'-demethoxyisoguaiacin (FIG. 7) were identified from the more lipophilic fraction FA (FIG. 5). These compounds have previously been described (Gisvold and Thaker, J. Pharm. Sci. 63:1905 (1974)). However, for the first time, the anti-HIV activity of all these cyclolignans is herein reported. For convenience, all the series of cyclolignans described in the legend of FIG. 7 are collectively termed "Rev.10:7" lignans.

EXAMPLE 6

Anti-HIV Activity of the Tricyclic Lignans

Tat-Mediated Transcription Inhibition

The activity of the Rev. 10:7 cyclolignans in inhibiting Tat-mediated transactivation of transcription from the HIV-1 LTR was measured using the SEAP assay described above. The results are shown in Table 3.

In Vitro Transcription Assay

The DNA used as template was the plasmid pLTR-1CAT, which contains HIV-LTR (−453 to +126) fused to the prokaryotic chloramphenicol acetyltransferase (CAT) gene. Unlabeled nucleoside triphosphates were from Pharmacia, and [α-$^{32}$P]UTP (400 Ci/mmol) from Amersham.

The DNA template for in vitro transcription was prepared by digesting 100 μg of plasmid pLTR-1CAT with a 10-fold unit excess of restriction enzyme EcoRI for 1–2 hours under buffer conditions suggested by the manufacturer (New England Biolabs). DNA digests were then subjected to twice phenol-chloroform-isoamyl alcohol (50:50:1) extractions and subsequently precipitated by ethanol. Hela whole-cell extracts (Manley extract) containing the polymerase and the transcription factors was prepared as previously described (Manley et al., *Proc. Acad. Sci. USA* 77:3855–3859 (1988)).

The transcription assay has been previously described (Bohan et al., *Gene Expression* 2:391–407 (1992)). Extracts prepared by the method of Manley, described above, (40 μg/reaction) and DNA template (0.4 μg/reaction) were pre-incubated with 0.4 μl of various concentrations of test compounds for 15 min at 30° C. The in vitro transcription buffer of Manley extract contained 10 mM HEPES (pH 7.9), 50 mM KCl, 0.5 mM EDTA, 1.5 mM DDT, 6.25 mM MgCl$_2$, and 8.5% glycerol. Unlabeled nucleoside triphosphates and [α-$^{32}$P]UTP (400 Ci/mmol) were mixed and added to the reaction mixture. The final volume of the reaction was brought to 15 μl followed by 1 hour incubation at 30° C. as illustrated in FIG. 9.

The transcription reaction was terminated by addition of 300 μl of stop solution (20 mM tris-HCl (pH 7.8), 150 mM NaCl, and 0.2% SDS), and extracted with equal volume of phenol. RNA in the aqueous phase was precipitated with 2.5 volumes of EtOH and 0.1 volume of 3 M sodium acetate. Following centrifugation, RNA pellets were washed with EtOH, dried and resuspended in 15 μl of denaturation mix containing 50% formamide:50% of 2×TBE, Xylene cyanol and bromophenol blue. The mixture was heated at 90° C. for 3 min, and electrophoresed at 400 V in 4% polyacrylamide (19:1 acrylamide:bisacrylamide) gel containing 7 M urea (prerun at 200 V for 30 min) and 1×TBE. The gel was exposed to Kodak XR-5 film at −70° C. with intensifying screens for autoradiography. The results of the assays are shown in FIG. 10. Table 4 illustrates the same results in numerical form after radioactivity counts of the 329 nt run off transcription spots.

Table 3

INHIBITION OF TAT-TRANSACTIVATION BY THE PURIFIED LIGNANS OF THE CREOSOTE BUSH INCLUDING CYCLOLIGNANS FB3 AND FB5 AS MEASURED BY SEAP ASSAY

| Test Compound | % Inhibition of Tat Transactivation | |
|---|---|---|
| | 10 μg/ml | 30 μg/ml |
| FB1 | 86* | 100 |
| | 82 | 99 |
| FB2 | 75 | 100 |
| | 86 | 100 |
| FB3 | 53 | 69 |
| | 22 | 59 |
| FB5 | 63 | 84 |
| | 63 | 87 |

(*)Samples were run in duplicate; each value is the mean of two determinations.

Table 4

IN VITRO INHIBITION OF THE HIV GENE TRANSCRIPTION BY PURIFIED LIGNANS INCLUDING CYCLOLIGNANS FB3 AND FB5.

| Lane | Test Cpds | Conc. (μg/ml) | CPM | % Transcription (% T) | % Inhibitor (100 -% T) |
|---|---|---|---|---|---|
| 1 | FB1 | 100 | 917 | 147 | 0 |
| 2 | | 120 | 804 | 129 | 0 |
| 3 | | 140 | N/A | — | >50* |
| 4 | FB2 | 100 | 972 | 155 | 0 |
| 5 | | 120 | 661 | 106 | 0 |
| 6 | | 140 | N/C | — | >90* |
| 7 | FB3 | 100 | 169 | 27 | 73 |
| 8 | | 120 | 55 | 9 | 91 |
| 9 | FB4 | 100 | 116 | 19 | 81 |
| 10 | | 120 | 47 | 8 | 92 |
| 11 | FB5 | 100 | 373 | 60 | 40 |
| 12 | | 120 | 264 | 42 | 58 |
| 13 | Control (DMSO) | — | 625 | 100 | — |

(*)Values were estimated from the Kodak film of gel after 3-day exposure

Inhibition of Human Immunodeficiency Virus Type 1 Integrase

Protein Purification. Wild-type HIV-1 integrase (HIV-1 IN) protein was obtained from Dr. R. Craigie. The protein was expressed in *Escherichia coli* and purified according to the procedure previously described by Sherman & Fyfe [*Proc. Natl. Acad. Sci. USA*, 87:5119–5123, 1990].

Oligonucleotide Substrates. Oligonucleotides containing the terminal sequence of HIV-1 DNA were synthesized and annealed to form the substrates (U5 29/29 oligonucleotides). Oligonucleotides were purified by ethanol precipitation and electrophoresis through 20% polyacrylamide (29:1 acrylamide:bisacrylamide) denaturing gels (7 M urea). The oligonucleotide samples were electroeluted from the sliced gels using the S&S ELUTRAP electroseparation system from Schleicher & Schuell.

Assay for integrase inhibition activity. Test materials (various extracts) were investigated for inhibitory activity of HIV-1 IN according to the procedure described by Han et al., *Biochemistry*, 34(32):10215–10223, 1995. One microgram of the appropriate oligonucleotide was $^{32}$P-labeled at the 5' termini by use of T4 polynucleotide kinase (New England Biolabs) and 25 μCi of adenosine [γ-$^{32}$P]-5'-triphosphate (3000 Ci/mmol, ICN). The labeled oligonucleotides were separated from unincorporated [γ-$^{32}$P]ATP using a Sephadex G-25 Quick Spin column (Boehringer Mannheim) and annealed with a 3-told molar excess of an unlabeled complementary strand in 10 mM Tris-HCl, pH 7.5, 1 mM EDTA, and 0.1 M NaCl. All the reaction mixtures for the IN protein-mediated cleavage reactions contained 25 mM HEPES, pH 7.5, 2.5 mM DTT, 50 mM NaCl, 5% glycerol (v/v), 7.5 mM Mg$^{2+}$ or Mn$^{2+}$, $^{32}$P-labeled substrates, and HIV-1 IN in a total volume of 20 μL.

Stock solutions of test materials were appropriately diluted in complete Assay Buffer to obtain the various concentrations of 10, 100, 300 μg/ml. One microliter (1 μl) of these solutions of test materials were pre-incubated with 0.4 μl integrase enzyme for 30 min on ice in 1×Assay Buffer at a final DMSO concentration of 5%. The $^{32}$P-labeled substrate (0.5 pmol double stranded 29 bp oligonucleotide) was then added and the reaction mixtures were incubated for additional 60 min at 37° C. as previously described (Mazumder et al., *Proc. Natl. Acad. Sci. USA*, 91:5771–5775, 1994). The reactions were stopped by the addition of an equal volume of stop solution (95% formamide, 30 mM EDTA, 0.1% xylene cyanol, and 0.1% bromophenol blue) to each sample, and the reactions were boiled for 5 min. A 10-μL aliquot of each reaction mixture was electrophoresed on a 7 M urea denaturing 18% polyacrylamide sequencing gel, and the reaction products were analyzed by autoradiography to visualize the cleavage of the 29 bp substrate. Quantitation of 3'-processing and strand transfer reaction products was performed with a PDI densitometer Model DNA 35 using a Kodak photographic step tablet for the calibration curve.

The results of the IN inhibition study are shown in FIG. 13. The Mes-7 extract of *Ambrosia deltoida* (AZ) shows a remarkable inhibition of HIV-1 integrase in a dose-responsive fashion.

The invention being thus described, various modifications of the materials and methods set forth above will be readily apparent to the practitioner of the invention of ordinary skill in the art. Such apparent modifications of the invention are to be considered as encompassed by the invention as claimed hereinbelow.

What is claimed is:

1. An extract composition having the following properties:

inhibits HIV-1 replication in vitro or in cultured cells;
    comprises at least one tricyclic compound
    inhibits Tat transactivation of transcription from the HIV-1 LTR in vitro with an $IC_{50} \leq 600$ μg/ml;
wherein said tricyclic compound is of the formula:

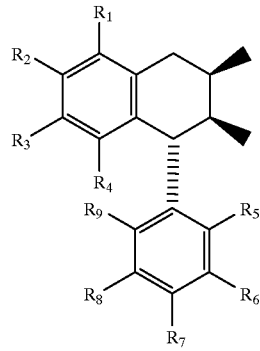

wherein at least three of $R_1$ through $R_9$ are hydroxyl or O-lower alkyl, at least one of $R_2$–$R_4$ is a hydroxyl, not all of $R_1$ through $R_9$ are hydroxyl, and those groups of $R_1$ through $R_9$ that are not hydroxyl or O-lower alkyl are hydrogen, O-methyl ester or O-ethyl ester.

2. The extract composition of claim 1, which is obtained from *Larrea tridentata*.

3. A compound of the formula:

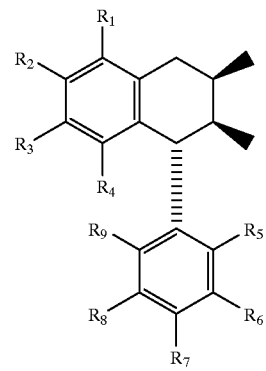

wherein at least three of $R_1$ through $R_9$ are hydroxyl or O-lower alkyl, at least one of $R_2$–$R_4$ is a hydroxyl, not all of $R_1$ through $R_9$ are hydroxyl, and those groups of $R_1$ through $R_9$ that are not hydroxyl or O-lower alkyl are hydrogen, O-methyl ester or O-ethyl ester.

4. The compound of claim 3, wherein $R_3$, $R_4$ and $R_7$ are all hydroxyl and $R_1$, $R_2$, $R_5$, $R_6$, $R_8$ and $R_9$ are all hydrogen.

5. The compound of claim 3, wherein $R_3$, $R_4$ and $R_7$ are all O-methyl and $R_1$, $R_2$, $R_5$, $R_6$, $R_8$ and $R_9$ are all hydrogen.

6. A method for treating a lentivirus infection comprising administering an amount of the compound of claim 3 effective for treating said lentivirus infection to a subject.

7. The extract of claim 1, wherein $R_3$, $R_4$ and $R_7$ are all hydroxyl and $R_1$, $R_2$, $R_5$, $R_6$, $R_8$ and $R_9$ are all hydrogen.

8. The extract of claim 1, wherein $R_3$, $R_4$ and $R_7$ are all O-methyl and $R_1$, $R_2$, $R_5$, $R_6$, $R_8$ and $R_9$ are all hydrogen.

9. A method for treating a lentivirus infection comprising administering an amount of the extract of claim 1 effective for treating said lentivirus infection to a subject.

* * * * *